(12) United States Patent
Chen et al.

(10) Patent No.: US 10,588,560 B2
(45) Date of Patent: Mar. 17, 2020

(54) SYSTEMS AND METHODS FOR FACILITATING EXERCISE MONITORING WITH REAL-TIME HEART RATE MONITORING AND MOTION ANALYSIS

(71) Applicant: CM HK Limited, Fortress Hill (HK)

(72) Inventors: Shih-Wei Chen, Taipei (TW); Ching-Lin Hsieh, Taipei (TW)

(73) Assignee: CM HK LIMITED, Fortress Hill (HK)

( * ) Notice: Subject to any disclaimer, the term of this patent is extended or adjusted under 35 U.S.C. 154(b) by 139 days.

(21) Appl. No.: 15/681,661

(22) Filed: Aug. 21, 2017

(65) Prior Publication Data

US 2018/0078192 A1 Mar. 22, 2018

Related U.S. Application Data

(60) Provisional application No. 62/397,357, filed on Sep. 21, 2016.

(51) Int. Cl.
| | |
|---|---|
| *A63B 24/00* | (2006.01) |
| *A61B 5/22* | (2006.01) |
| *A61B 5/11* | (2006.01) |
| *A61B 5/00* | (2006.01) |
| *G16H 20/30* | (2018.01) |
| *G16H 40/63* | (2018.01) |
| *A61B 5/0205* | (2006.01) |

(52) U.S. Cl.
CPC ............ *A61B 5/222* (2013.01); *A61B 5/0205* (2013.01); *A61B 5/11* (2013.01); *A61B 5/1116* (2013.01); *A61B 5/1118* (2013.01); *A61B 5/4866* (2013.01); *A61B 5/7275* (2013.01); *G16H 20/30* (2018.01); *G16H 40/63* (2018.01); *A61B 5/681* (2013.01); *A61B 2562/0219* (2013.01); *A63B 2220/836* (2013.01)

(58) Field of Classification Search
None
See application file for complete search history.

(56) References Cited

U.S. PATENT DOCUMENTS

| | | | |
|---|---|---|---|
| 8,920,332 | B2 | 12/2014 | Hong et al. |
| 8,998,815 | B2 | 4/2015 | Venkatraman et al. |
| (Continued) | | | |

*Primary Examiner* — Etsub D Berhanu
(74) *Attorney, Agent, or Firm* — McClure, Qualey & Rodack, LLP

(57) ABSTRACT

Systems and methods for facilitating exercise monitoring are provided. A representative method includes: using a processor, having processor circuitry, to: obtain motion readings reported from an inertial sensor of a wearable device and corresponding to a scheduled training types; receive the schedule and a target status of a target training count or a target training time corresponding to each of the training types; determine the current training type based on the schedule; select one of the computing models based on the current training type; compare the set of matching characteristics corresponding to the current training type and the motion readings until the target status has been attained for the current training type; select a next training type based on the schedule; select another one of the computing models based on the next training type; determine activity information associated with the schedule; and compute an exercise amount of the user based on the target status, the activity information, and the schedule.

20 Claims, 11 Drawing Sheets

(56) References Cited

U.S. PATENT DOCUMENTS

| | | | |
|---|---|---|---|
| 2005/0033200 A1* | 2/2005 | Soehren | A61B 5/0002 |
| | | | 600/595 |
| 2005/0202934 A1* | 9/2005 | Olrik | A63B 24/0062 |
| | | | 482/8 |
| 2010/0056872 A1* | 3/2010 | Kahn | A61B 5/1038 |
| | | | 600/300 |
| 2011/0054270 A1* | 3/2011 | Derchak | A61B 5/0002 |
| | | | 600/300 |
| 2014/0073486 A1 | 3/2014 | Ahmed et al. | |
| 2014/0163704 A1* | 6/2014 | DePietro | A43B 3/0005 |
| | | | 700/91 |
| 2016/0058302 A1* | 3/2016 | Raghuram | A61B 5/0205 |
| | | | 600/301 |
| 2016/0058372 A1 | 3/2016 | Raghuram et al. | |
| 2017/0087414 A1 | 3/2017 | Aragones et al. | |
| 2017/0173394 A1* | 6/2017 | Rider | A63B 24/0075 |
| 2018/0169474 A1* | 6/2018 | Reddy | A63B 24/0062 |

\* cited by examiner

SYSTEMS AND METHODS FOR FACILITATING EXERCISE MONITORING WITH REAL-TIME HEART RATE MONITORING AND MOTION ANALYSIS

CROSS REFERENCE TO RELATED APPLICATION

This utility application claims the benefit of and priority to U.S. provisional application 62/397,357, filed on 21 Sep. 2016, the entirety of which is incorporated by reference herein.

BACKGROUND

Technical Field

The disclosure relates to the monitoring of exercise based on real-time heart rate monitoring and/or motion analysis.

Description of the Related Art

Various devices incorporate sensors that determine motion associated with the devices, including wearable devices that are worn by a user (e.g., a smart watch). Many of these devices tend to offer perceived advantages, such as convenience of use. Unfortunately, these devices suffer from an inability to provide detailed information to a user engaging in numerous physical activities or exercises. Thus, there is a need to provide solutions that address these technical shortcomings.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1:
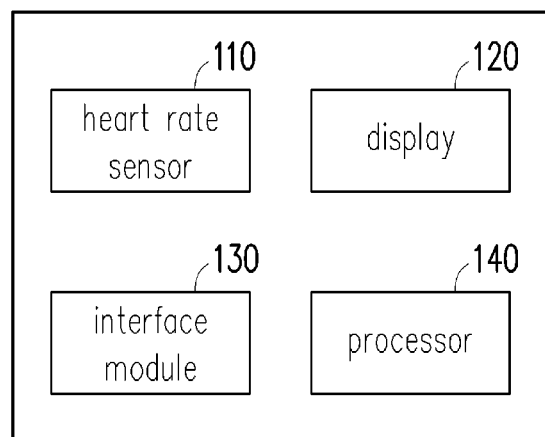
FIG. 1 illustrates a proposed system in accordance with one of the exemplary embodiments of the disclosure.

Some embodiments of the disclosure will now be described more fully hereinafter with reference to the accompanying drawings, in which some, but not all embodiments of the application, are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a proposed system in accordance with one of the exemplary embodiments of the disclosure. All components of the system and their configurations are first introduced in FIG. 1. The functionalities of the components are disclosed in more detail in conjunction with FIG. 2.

Referring to FIG. 1, for exemplary purposes, a proposed system 100 may include a heart rate sensor 110, a display 120, an interface module 130, and a processor 140. Clearly, each of the aforementioned components incorporates associated circuitry (e.g., sensor circuitry, display circuitry, interface circuitry, and processor circuitry, although such circuitry is not depicted in FIG. 1) for performing related functions.

The heart rate sensor 110 may be a device that measures the heart rate of an individual in real-time by various approaches. For exemplary purposes, the heart rate sensor 110 may be a photoplethymography (PPG) device to estimate the skin blood flow per unit length change using infrared light. Other approaches such as pneumatic plethysmography, impedance cardiography, phonocardiography, electrocardiography which are well-known per se may also be used.

The display 120 may display text or graphic information. For exemplary purposes, the display 120 may be a liquid crystal display (LCD), a light-emitting diode (LED) display, a field emission display (FED), a plasma display, a quantum dot display, and so forth.

The interface module 130 may be an input device that receives touch-based inputs from the user. For exemplary purposes, the interface module 130 may be a pointer device (e.g. a mouse), a keyboard, physical buttons, a remote control, and so forth. Alternatively, the interface module 130 may incorporate touch detection components arranged in rows and columns in the display 120 for detecting touch inputs by a finger or other objects. The touch detection components may be, for example, capacitive touch detection components, surface acoustic wave touch detection components, electromagnetic touch detection components, or near-field imaging touch detection components.

The processor 140 may process data obtained from the heart rate sensor 110 so as to perform the proposed method. The processor 140 may include one or more of a North Bridge, a South Bridge, a field programmable array (FPGA), a programmable logic device (PLD), an application specific integrated circuit (ASIC), or other similar device or a combination thereof. The processor 140 may also include a central processing unit (CPU), a programmable general purpose or special purpose microprocessor, a digital signal processor (DSP), an application processor, a baseband processor, a wireless processor, an application specific integrated circuit (ASIC), a programmable logic device (PLD), or other similar devices or a combination thereof.

It should also be appreciated that a memory (not shown) may be included in the proposed system 100 as well. The memory may include various forms of non-transitory, volatile, and non-volatile memories such as one or a combination of a stationary or mobile random access memory (RAM), a read-only memory (ROM), a flash memory, a hard drive or other similar devices or interfaces. The memory can store application programs, codes, or instructions to perform the proposed method as well as real-time data collected from the heart rate sensor 110.

In an exemplary embodiment, the heart rate sensor 110 may be implemented as a wearable device to be worn around the user's wrist such as a watch, a wristband, a health bracelet, and so forth. The display 120, the interface module 130, and the processor 140 may be implemented as a companion device paired with the wearable device, such as a smart phone, a laptop computer, a tabular computer, or a desktop computer, to receive data from the wearable device. The wearable device and the companion device may include communication interfaces (not shown) such as wired (e.g. Ethernet and USB) or wireless (e.g. WLAN, Bluetooth, NFC, cellular, Wifi) circuitry and protocols for data transmission. In some embodiments, the wearable device may transmit raw measurement data to the companion device without further processing. The companion device may carry out a determined function to process the raw measurement data with flexibility and open integration. In other embodiments, the wearable device may be programmed or hardwired to perform pre-processing on the raw measurement data to extract certain characteristics to reduce data transmission burden. In another exemplary embodiment, the system 100 may be implemented as a standalone wearable device. The disclosure is not limited in this regard.

Figure 2:
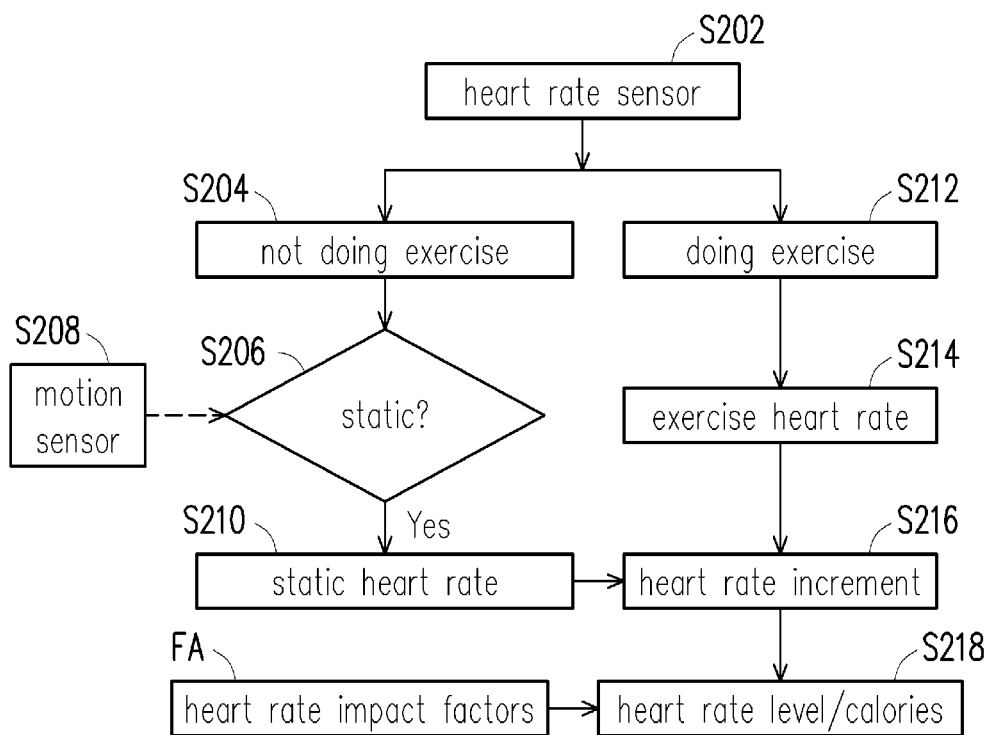
FIG. 2 illustrates a flowchart of a proposed method in accordance with one of the exemplary embodiments of the disclosure.

FIG. 2 illustrates a flowchart of a proposed method from the perspective of heart rate in accordance with one of the exemplary embodiments of the disclosure. The steps of FIG. 2 could be implemented by the proposed system 100 as illustrated in FIG. 1.

Referring to FIG. 2 in conjunction with FIG. 1, the heart rate sensor 110 may be triggered for heart rate measurement (Step S202), where the heart rate may be categorized into a static heart rate and an exercise heart rate. The static heart rate is referred to as a heart rate measured by the heart rate sensor 110 when the user is not doing exercise (S204) and substantially in a static state, and it is also known as an at-rest heart rate. In an exemplary embodiment, the determination of whether the user is in the static state (S206) may rely on a measurement through an extra motion sensor (S208). If so, the processor 140 may set such measurement as the static heart rate (S210). In another exemplary embodiment, a message may be shown on the display 120 to instruct the user to sit or stand still for static heart rate measurement. Yet in another exemplary embodiment, the processor 140 may simply retrieve the user's historical measurement or a normal at-rest heart rate of individuals at the same age as the user and set that rate as the static heart rate measurement.

On the other hand, the exercise heart rate is referred to as a heart rate measured by the heart rate sensor 110 when the user is doing exercise (S212). Once the processor 140 obtains the exercise heart rate of the user (S214), it may compute a heart rate increment based on the static heart rate and the exercise heart rate (S216) and further convert the heart rate increment to a heart rate level and/or calories (S218) for informing the user. The conversion may be dependent upon some heart rate impact factors (FA) such as physiological parameters (e.g. age, gender, weight, height, body mass index), past medical history, recent exercise data, and so forth.

In an exemplary embodiment, the processor 140 may compute overall statistics including a heart rate level and/or calories for the entire interval training session. The processor 140 may also compute individual statistics including a heart rate level and/or calories for each interval training cycle. It should also be noted that, any instantaneous measured or computed data such as exercise heart rate, calories burned, exercise time elapsed may be displayed in textual or graphical form during the session.

Figure 3:
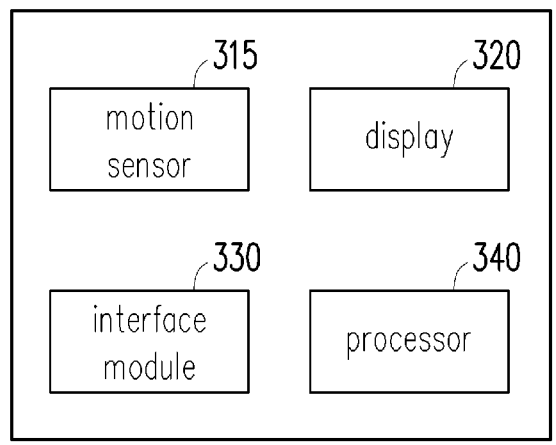
FIG. 3 illustrates a proposed system in accordance with one of the exemplary embodiments of the disclosure.

FIG. 3 illustrates a proposed system in accordance with one of the exemplary embodiments of the disclosure. All components of the system and their configurations are introduced in FIG. 3. The functionalities of the components are disclosed in more detail in conjunction with FIG. 4.

Referring to FIG. 3, for exemplary purposes, a proposed system 300 may include a motion sensor 315, a display 320, an interface module 330, and a processor 340, wherein similar components to FIG. 1 are designated with similar numbers having a "3" prefix.

The motion sensor 315 may be one or more inertial sensors implemented in a wearable device that detect events or changes in the user's position and provides a corresponding output in a relative basis. For exemplary purposes, in the present exemplary embodiment, the motion sensor 315 may be one or a combination of an accelerometer (e.g. G-sensor), a gyroscope (e.g. gyro-sensor), or any sensor that detects the linear movement, the direction of the linear movement, or the rotational movement of the wearable device. For example, a three-axis accelerometer would output acceleration data corresponding to each (x-y-z) axis in response to any detection of a sudden movement when the wearable device encounters an external force. A gyroscope would detect a rotational movement of the wearable device rotating about a particular axis in space and output data representing the rotational movement. A combination of the accelerometer and the gyroscope may create a more accurate measurement of an overall movement and orientation of the wearable device.

Figure 4:
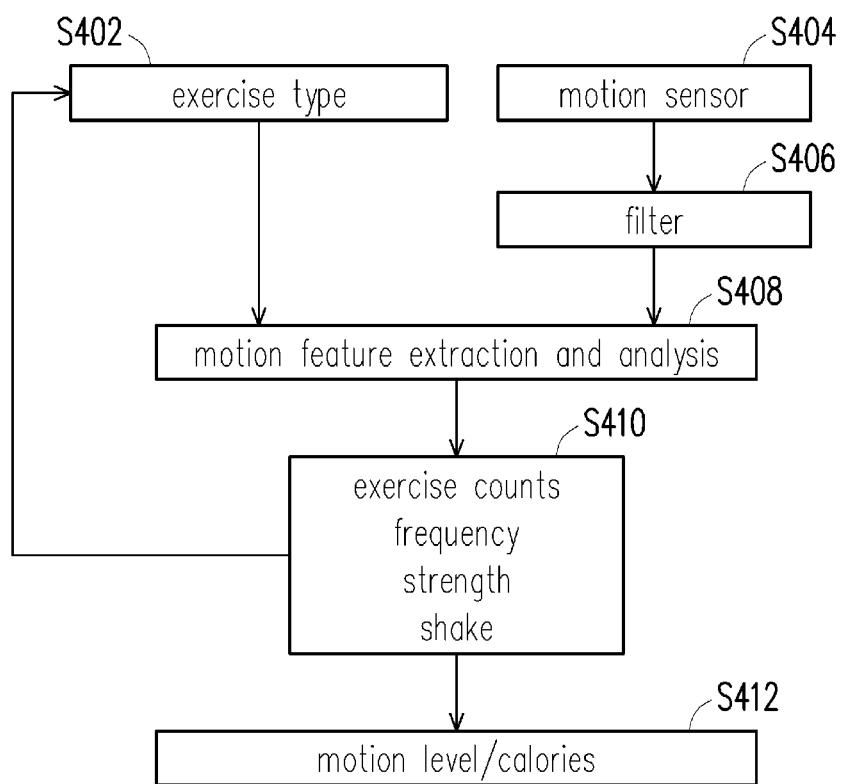
FIG. 4 illustrates a flowchart of a proposed method in accordance with one of the exemplary embodiments of the disclosure.

FIG. 4 illustrates a flowchart of a proposed method from the perspective of motion in accordance with one of the exemplary embodiments of the disclosure. The steps of FIG. 4 could be implemented by the proposed system 300 as illustrated in FIG. 3.

It should first be noted that, before iterations start, the processor 340 may obtain a training list (or schedule) containing exercise (training) types for exercising (e.g., interval training). In the present exemplary embodiment, such training list may be defined by the user through the interface 330. For example, the system 300 may store types of low-intensity and high-intensity exercises suitable for interval training such as push-ups, crunches, squats, lunges, sprints, burpees, and jumping jacks, for example. Each exercise type stored in the system 300 may be described by a corresponding descriptive computing model including graphical or numerical features such as, for example, mean, standard deviation, wave amplitude, length, frequency, histogram in terms of distance, velocity, acceleration, and/or intensity in a time domain. The user may add preferred exercise types interspersed with relief/rest periods to the training list. In other exemplary embodiments, such a training list may be selected from the user's historical training lists, professional training lists pre-stored in the system 300 or available from the Internet.

Now referring to FIG. 4 in conjunction with FIG. 3, the processor 340 may report a current exercise type according to the training list (S402). Meanwhile, the motion sensor 315 may be triggered (S404), and the processor 340 may start obtaining motion data from the motion sensor 315 and filter out noise and outliers through the use of filters (S406) such as a high-pass filter, a low-pass filter, a moving mean filter, a noise filter, and so forth. The processor 340 may perform motion feature extraction and analysis on the filtered motion data (S408) according to the descriptive computing model of the current exercise type so as to identify mode, posture, power, distance, and/or standard deviation, for example. Since the current exercise type has already been reported, the processor 340 may be able to determine exercise counts, frequency, strength, and/or shake that may categorize the user's exercise intensity with respect to the current exercise type according to its descriptive model as well (S410).

In the present exemplary embodiment, the exercise intensity may be based on exercise counts within a predefined time period. For example, if the current exercise type is push-ups, the processor 340 may determine the number of repeated changes in posture within the predefined time period. If the current exercise type is jumping jacks, the processor 340 may determine the number of repeated changes in strength within the predefined time period. If the current exercise type is squats, the processor 340 may determine repeated changes in distance within the predefined time period.

Next, the processor 340 may then convert such exercise intensity to a motion level and/or calories (S412) for the user. The processor 340 may then move on to a next exercise type to start another iteration after being reported. The processor 340 may report when a preset exercise time of the current exercise type is up or when a preset exercise count of the current exercise type has been reached.

Similarly, in an exemplary embodiment, the processor 340 may compute overall statistics including a motion level and/or calories for the entire interval training session. The processor 340 may also compute individual statistics including a motion level and/or calories for each interval training cycle or even each exercise type. It should also be noted that, any instantaneous measured or computed data such as histogram, motion level, calories burned, exercise time elapsed may be displayed in textual or graphical form.

Figure 5:
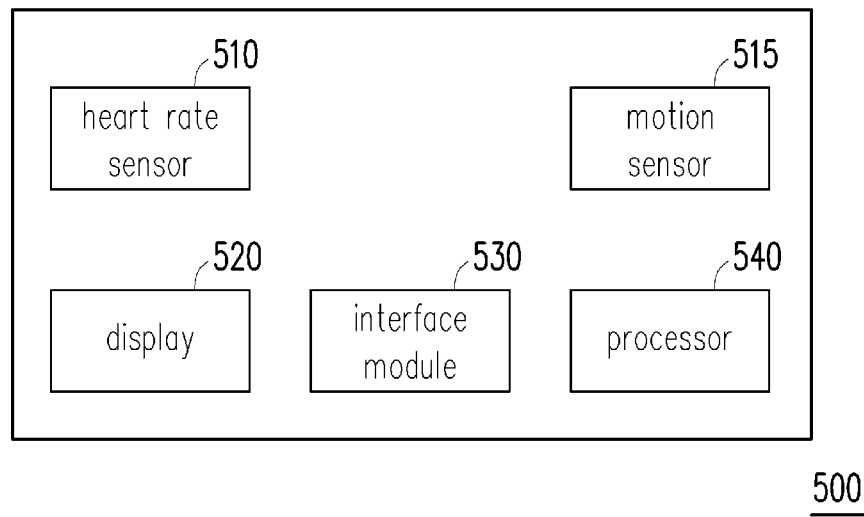
FIG. 5 illustrates a proposed system in accordance with one of the exemplary embodiments of the disclosure.

The functionality and/or components of system 100 and system 300 may be integrated into a single system. By way of example, FIG. 5 illustrates a proposed system in accordance with one of the exemplary embodiments of the disclosure. All components of the system and their configurations are introduced in FIG. 5. The functionalities of the components are disclosed in more detail in conjunction with FIG. 6 as well as FIG. 7.

Referring to FIG. 5, for exemplary purposes, a proposed system 500 may include a heart rate sensor 510, a motion sensor 515, a display 520, an interface module 530, and a processor 540, wherein similar components to FIG. 1 and FIG. 3 are designated with similar numbers having a "5" prefix.

Figure 6:
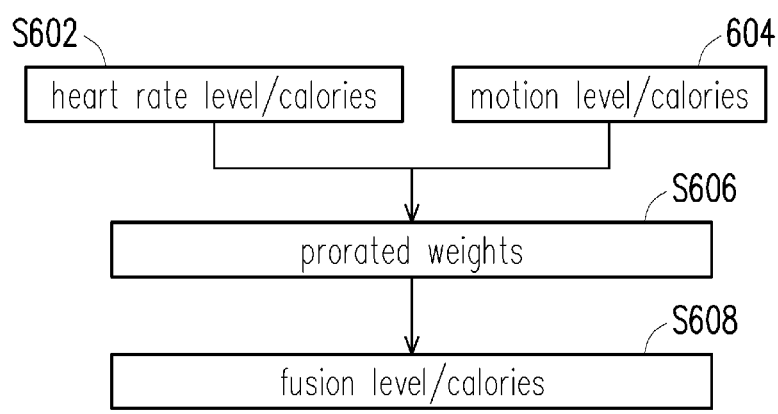
FIG. 6 illustrates a flowchart of a proposed method in accordance with one of the exemplary embodiments of the disclosure.

FIG. 6 illustrates a flowchart of a proposed method from the perspective of both heart rate and motion in accordance with one of the exemplary embodiments of the disclosure. The steps of FIG. 6 could be implemented by the proposed system 500 as illustrated in FIG. 5.

Referring to FIG. 6 in conjunction with FIG. 5, from a generalized perspective, the processor 540 may obtain a heart rate level and/or calories (referred to as "heart rate training data") from the heart rate sensor 510 (S602) and a motion level and/or calories (referred to as "motion training data") from the motion sensor 515 (S604) corresponding to a current exercise type. It should be noted that, prior to S602 and S604, the processor 540 may perform steps similar to S202-S218 in FIG. 2 and S402-S412 in FIG. 4. In other words, S602 and S604 may be viewed as continuous steps of S216/S218 and S412.

Next, the processor 540 may perform fusion on the heart rate training data and the motion training data according to given prorated weights (S606) to produce fusion level/calories (referred to as "fusion training data") for a more robust measurement (S608). For example, the processor 540 may compute a weighted average of the heart rate level and the motion level. The prorated weights assigned to the heart rate level and the motion level may vary based on exercise types. In some exemplary embodiments, the prorated weights may also be associated with genders, ages, and etc.

Figure 7:
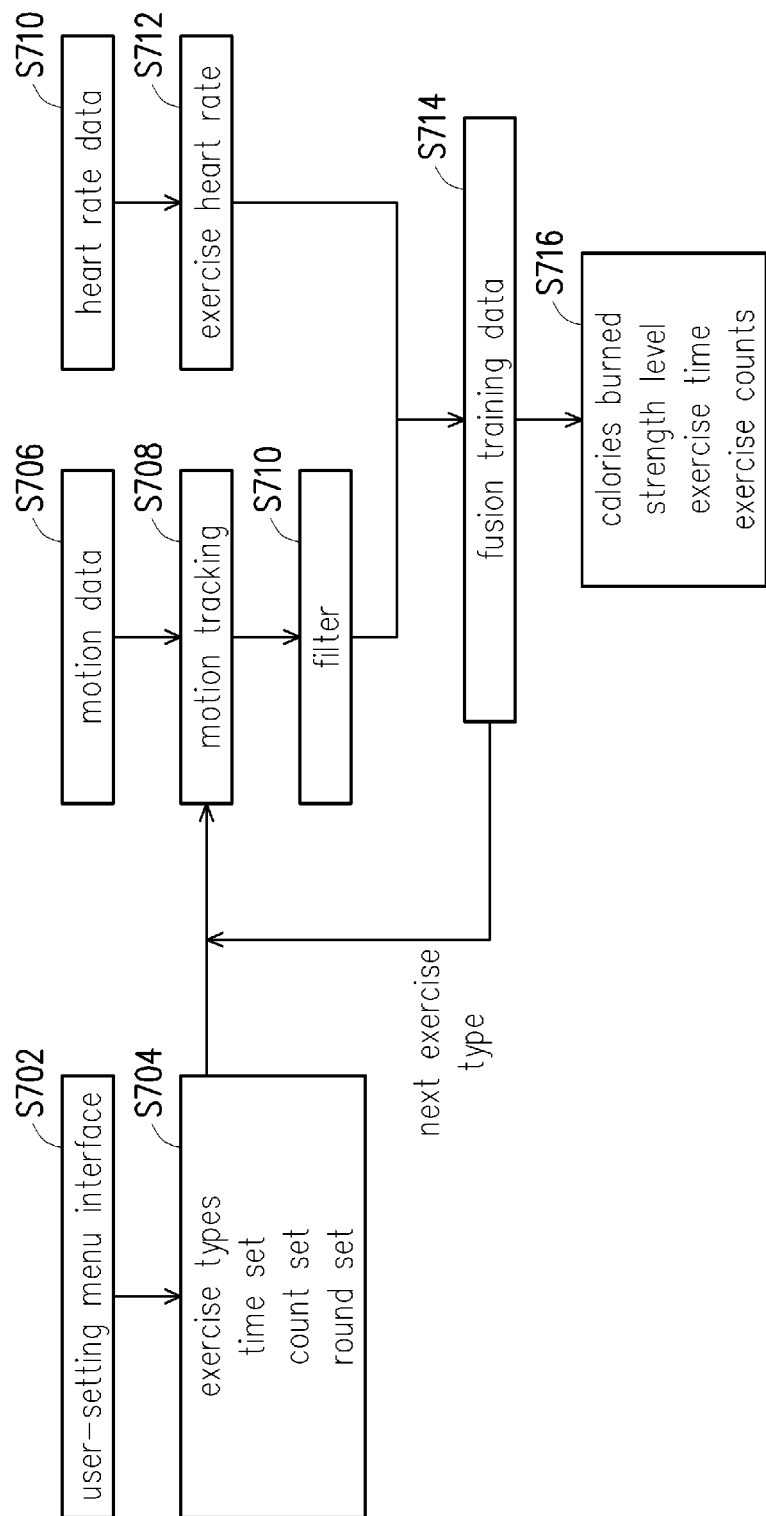
FIG. 7 illustrates a flowchart of a proposed method in accordance with one of the exemplary embodiments of the disclosure.

FIG. 7 illustrates a flowchart of a proposed method from the perspective of both heart rate and motion in accordance with one of the exemplary embodiments of the disclosure. The steps of FIG. 7 could be implemented by the proposed system 500 as illustrated in FIG. 5.

Referring to FIG. 7 in conjunction with FIG. 5, from a more detailed perspective, the processor 540 may display a user-setting menu interface on the display 520 (S702) which allows the user to define his own interval training session through the interface module 530. In the present exemplary embodiment, the user may first select either a time mode (i.e. training time basis) or a count mode (i.e. repeated count basis), build his own training list including multiple exercise types, and set training time, the number of training counts and/or training rounds. (S704). The processor 540 may then obtain the aforesaid user settings and start the interval training session. That is, the processor 340 may report a current exercise type according to the training list.

The processor 540 may start obtaining motion data from the motion sensor 515 (S706) and perform motion tracking through feature extraction and analysis (S708) as in S406-S408 in FIG. 4 to compute motion training data. Meanwhile, the processor 540 may also start obtaining heart rate data from the heart rate sensor 510 (S710) and determine an exercise heart rate (S712) to determine heart rate training data.

The processor 540 may next perform fusion on the heart rate training data and the motion training data to produce fusion training data (S714) and output calories burned, strength level, exercise time, and exercise counts corresponding to the current exercise type (S716). The processor 540 may move on to a next exercise type once the current exercise type has been completed.

In the present exemplary embodiment, the heart rate training data is considered as auxiliary information for a more robust measurement. The processor 540 may calculate calories burned and strength level for each exercise type according to the exercise counts and exercise time on the motion basis. Next, the processor 540 may calibrate the calculated calories burned and the calculated strength level based on the heart rate on the heart rate basis. In the time mode, the exercise time indicates the total training time being set, and the exercise counts indicate the number of repeated counts within such training time. In the count mode, the exercise counts indicate the total number of training counts being set, and the exercise time indicates the time elapsed after such training counts have been reached.

Figure 8:
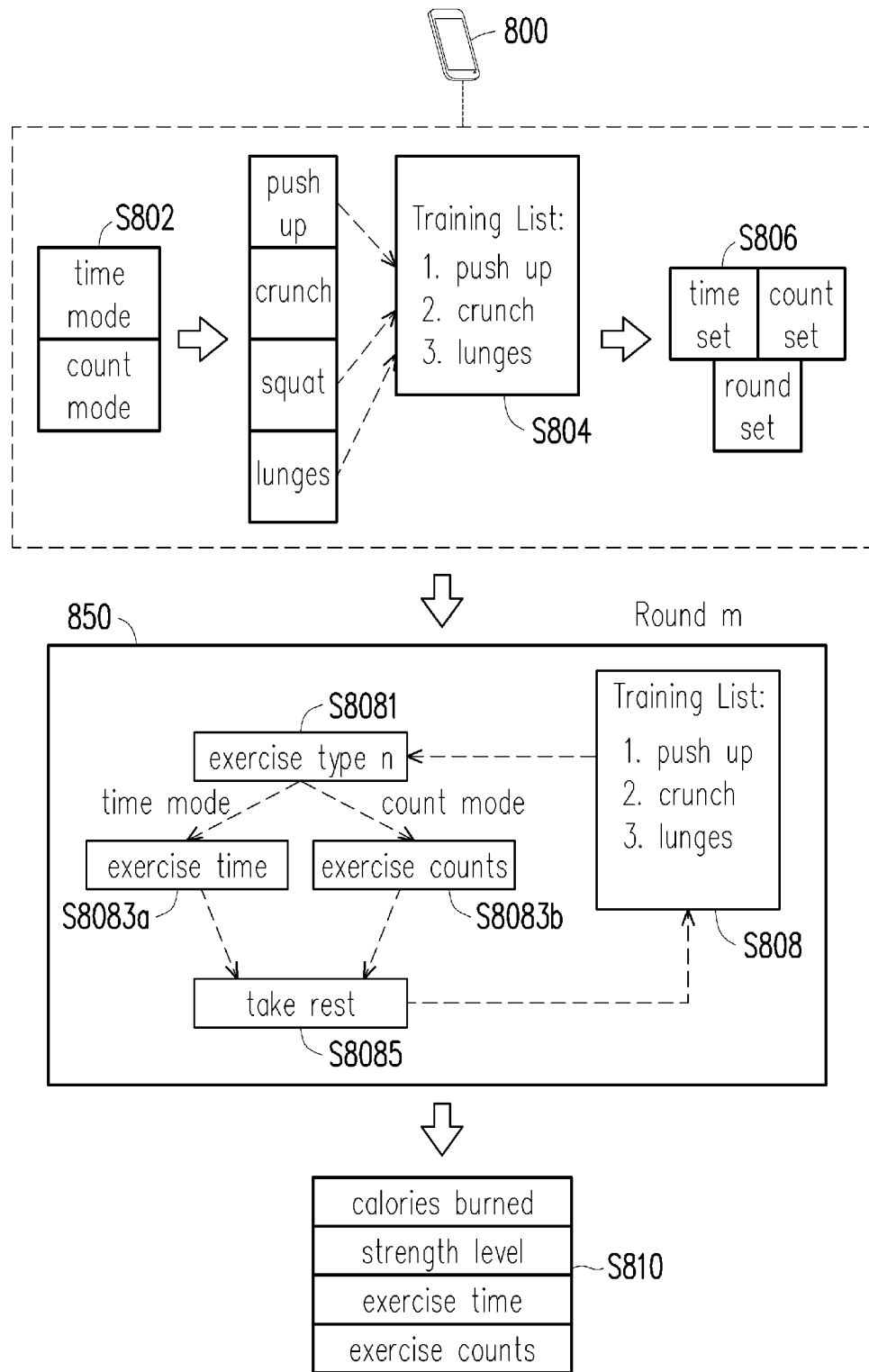
FIG. 8 illustrates a functional flowchart of a proposed method in accordance with one of the exemplary embodiments of the disclosure.

FIG. 8 illustrates a functional flowchart of a proposed method in accordance with one of the exemplary embodiments of the disclosure. The steps of FIG. 8 could be implemented by the proposed system 500 as illustrated in FIG. 5.

Referring to FIG. 8 in conjunction with FIG. 5, the user may be provided to set up an interval training session through a companion device 800 (e.g. a smart phone) paired with a wearable device 850 (e.g. a watch).

The user may first select either a time mode or a count mode to define the type of training cycle (round) (S802) and then select and arrange the order of exercise types to build a training list (S804). In this exemplary embodiment, the training list may include push-ups, crunches, and lunges. Next, the user sets a training time, the number of training counts and/or training rounds (S806), and the interval training session may start (S808). From the perspective of the system 500, the processor 540 may receive a time/count mode selection, a training list, and the settings of the training time, the number of training counts and/or training rounds upon user setting through the interface module 530 before the interval training session starts. It should be noted that, the order of S802-S806 may be modified. For example, the training list in S804 may be built before mode selection as in S802 and training settings as in S806. The disclosure is not limited in this regard.

The interval training session may start from the first exercise type on the training list (S8081), accumulate exercise time (S8083a) or exercise counts (S8083b) for the first exercise type, enter the relief/rest period (e.g. 20 seconds) once the first exercise type ends (S8085), and then move on to the next exercise type on the training list. As an example, S808 indicates that the current round is m and the current exercise type is n. From the perspective of the system 500, S8081-S8085 may be performed by the processor 540 according to the selection and the settings received in S802-S806. After each exercise type has been completed, the interval training session may move on to the next round and restart from the first exercise type on the training list. It should be noted that information such as the training list including the current exercise type, the accumulated exercise time, and the accumulated exercise counts may be displayed throughout the entire interval training session.

When the user has completed all the rounds, a training result such as calories burned, strength level, exercise time, and exercise counts may be displayed (S810). That is, the processor 540 may control the display 520 to display the training result. The training result may also be broken down into each individual round or each exercise type to provide the user a straightforward visualization on any specific workout.

Figure 9:
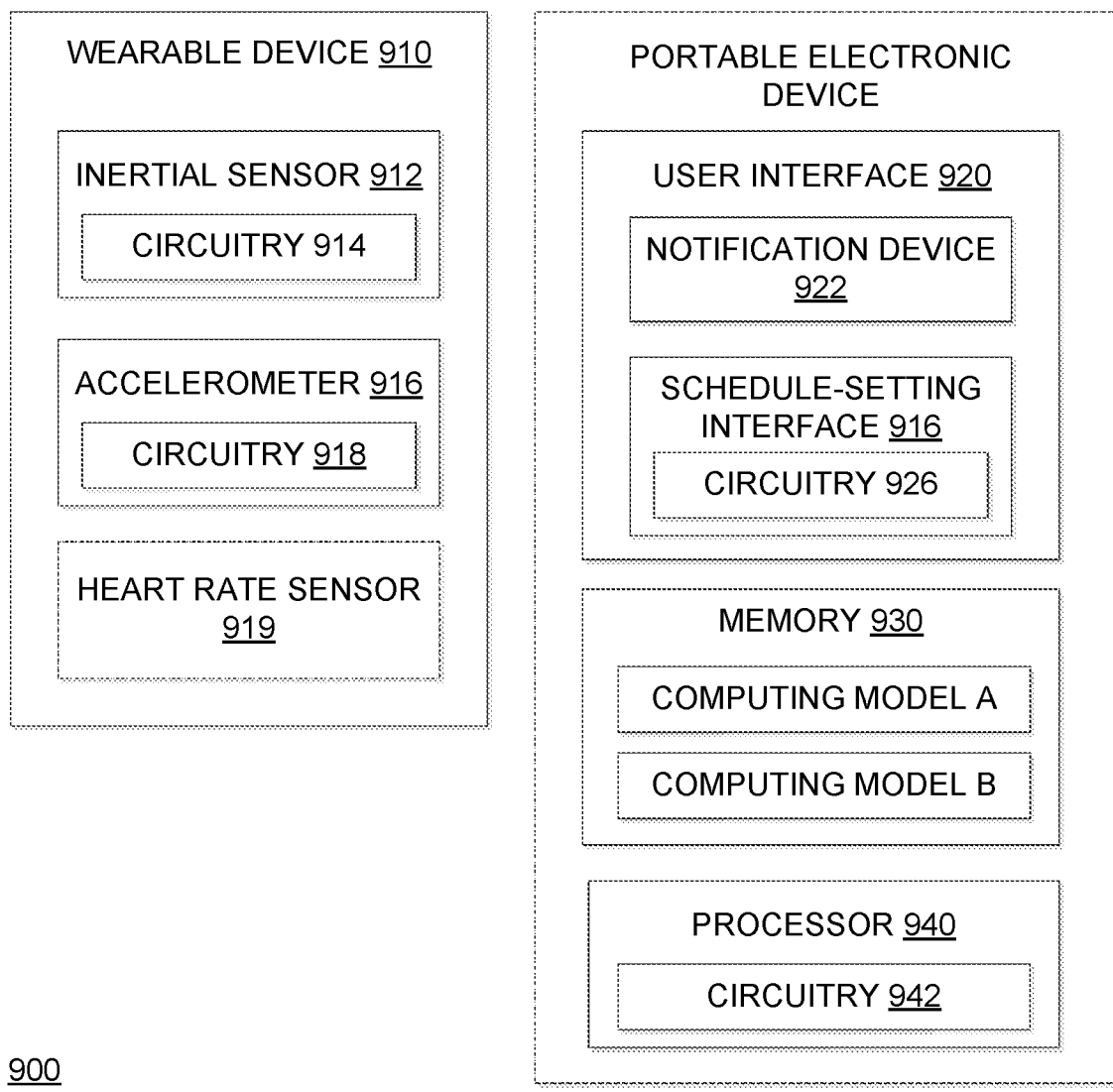
FIG. 9 illustrates a proposed system in accordance with one of the exemplary embodiments of the disclosure.

FIG. 9 illustrates a proposed system in accordance with one of the exemplary embodiments of the disclosure. As shown in FIG. 9, for exemplary purposes, a proposed system 900 may include a wearable device 910 (e.g., a smart watch, smart band, etc.) that is configured to be worn by a user. Wearable device 910 incorporates an inertial sensor 912, which includes inertial sensor circuitry 914. Inertial sensor 912 is configured to report motion readings based on motion of the inertial sensor. Inertial sensor 912 also incorporates an accelerometer 916, which includes accelerometer circuitry 918. Accelerometer 916 is configured to generate accelerometer readings based on accelerations of the accelerometer. An optional heart rate sensor 919 with associated heart rate sensor circuitry (not shown) also may be provided in some embodiments.

System 900 also includes a user interface 920, a memory 930, and a processor 940, each of which may be carried by the wearable device in some embodiments. It should be noted that the wearable device 910 can be a single device configured to be worn on only one of the upper body or the lower body of the user. With assistance from the schedule-setting interface 924, the processor 940 can determine which one of the at least two full-body training types is being performed by the user without an additional wearable device being worn on another portion of the user (e.g., on the other of the upper body and the lower body). In some embodiments, one or more of user interface 920, memory 930, and processor 940 may be carried by another device, such as a portable electronic device (e.g., a smartphone).

User interface 920 includes a notification device 922 (e.g., a display, speaker, or haptic device) and a schedule-setting interface 924 (e.g., a touch pad, keyboard). In particular, schedule-setting interface 924, which includes schedule-setting interface circuitry 926, is configured to provide a schedule of training types for use by the user and, in some embodiments, may be capable of being set by a local/remote user, coach, and/or fitness program provider. Notification device 922 is configured to provide a notification to the user based on the schedule of training types. In some embodiments, the notification includes information corresponding to a current training type from the schedule. In this regard, in some embodiments, the training types including at least two full-body training types, each of which is associated with exercising both the upper body and the lower body of the user. By way of example, full-body training types include squats and burpees, among numerous others.

Memory 930 is configured to store one or more computing models (e.g., computing model A, computing model B), each of which defines a set of matching characteristics associated with a respective one of the training types. Specifically, each set of matching characteristics may include, but is not limited to, one or more of: the user exhibiting a specific posture/orientation, which can be calculated based on acceleration readings (accelerometer), rotation readings (gyroscope), and/or magnetometer readings; the user retaining the same posture/orientation over a specific time, which may be calculated based on a small variance of acceleration readings (e.g., a variance under a threshold value) over a predetermined time; the user exhibiting a rapid posture change; the user exhibiting a movement vector toward a direction (e.g., sum acceleration is much lower/higher than gravity acceleration and the decrease/increase is present along the same axis for a predetermined time); and, the user exhibits an impact pattern (e.g., fall on the ground after jumping, hand claps, or push-ups on the ground). In some embodiments, the sets of matching characteristics associated with at least two of the full-body training types share a common vector (referred to as a "common determination vector") associated with the acceleration readings. It should also be noted that a determination threshold can be different for the two sets of matching characteristics. For instance, two different degrees of de-acceleration may be provided.

Processor 940, which includes processor circuitry 942, is configured to: obtain the motion readings reported from the inertial sensor and corresponding to the scheduled training types; receive the schedule of training types and a target status of a target training count or a target training time corresponding to each of the training types; and, determine the current training type based on the schedule of training types. Based on the current training type, the processor is further configured to: select one of the computing models; and, compare the set of matching characteristics corresponding to the current training type and the motion readings until the target status has been attained for the current training type. Thereafter, the processor is configured to: select a next training type based on the schedule of training types; select another one of the computing models based on the next training type; determine activity information (e.g., heart rate, moving strength, body temperature) associated with the schedule of training types; and, compute an exercise amount of the user (e.g., exercise strength, calories burned) based on the target status, the activity information, and the schedule of training types. In some embodiments, the exercise amount is expressed with respect to exercise strength or calories consumed exhibited by the upper body and by the lower body of the user.

In some embodiments, if the target status is a target training count, the processor may be further configured to compare the set of matching characteristics corresponding to the current training type and the motion readings to determine a count based on a number of times the motion readings exhibit a matching pattern to the matching characteristics. Then, the activity information may include an exercise time during which the count accumulates and reaches the target training count.

In contrast, if the target status is a target training time, the processor may be further configured to compare the motion readings reported during the target training time and the set of matching characteristics corresponding to the current training type to determine a count based on a number of times the motion readings exhibit a matching pattern to the matching characteristics during the target training time. The activity information may then include the count determined.

In some embodiments, computing of the exercise amount when the current training type is a full-body training type may include the processor being configured to: compare the acceleration readings with the common determination vector and a determination threshold according to the selected one of the computing models corresponding to the current training type to provide a comparing result. In such an embodiment, an accumulated trigger count may be incremented if the comparing result is positive unless a freeze condition occurs. In this regard, a freeze condition corresponds to consecutive positive comparing results occurring within a freeze time threshold. In this manner, the freeze condition indicates that the user may be cheating (i.e., attempting to circumvent the detection scheme of the system to achieve a training result prematurely). The exercise amount may then be computed, with respect to the current training type, based on the accumulated trigger count or the training time and the current training type.

Figure 10:
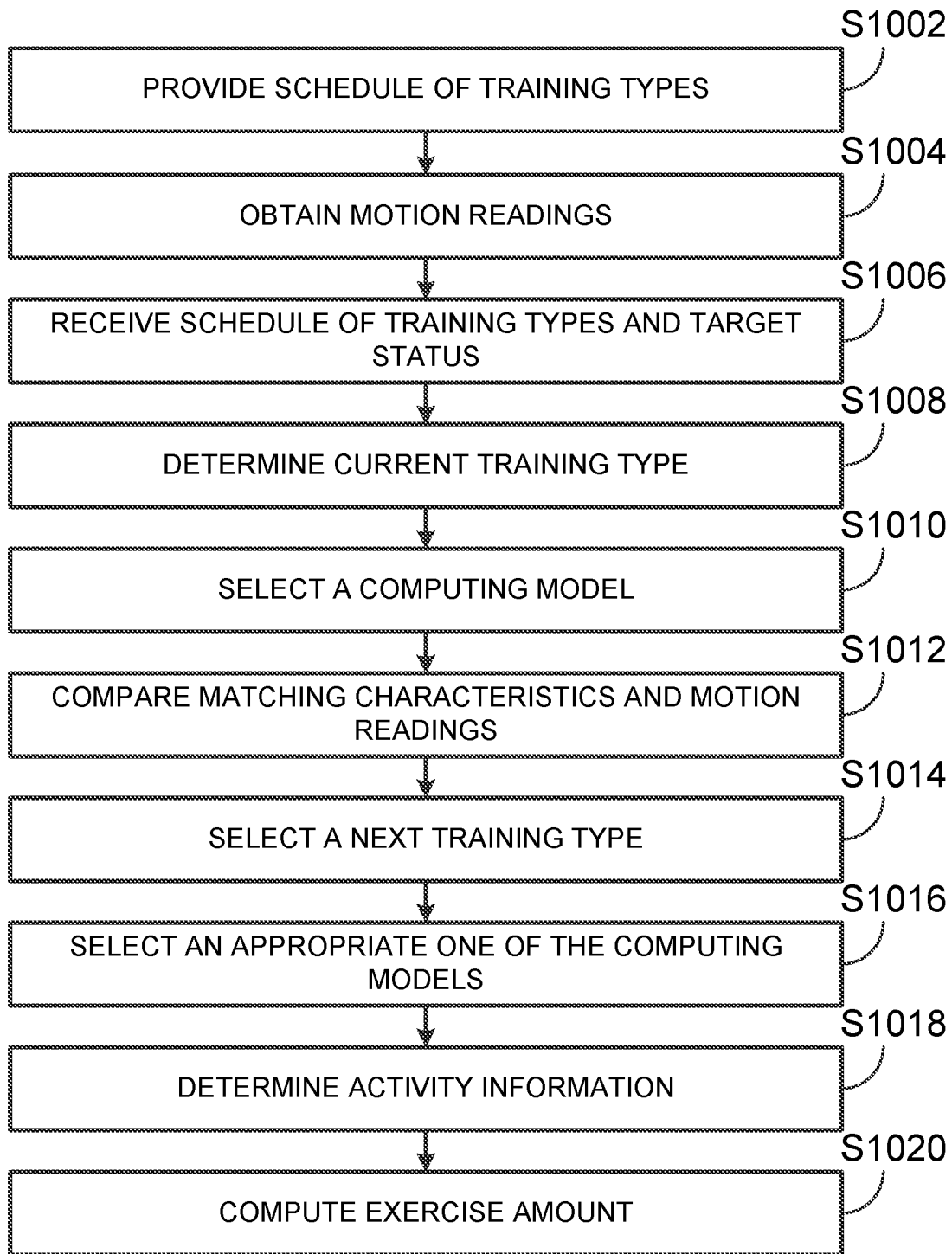
FIG. 10 illustrates a functional flowchart of a proposed method in accordance with one of the exemplary embodiments of the disclosure.

FIG. 10 illustrates a functional flowchart of a proposed method in accordance with one of the exemplary embodiments of the disclosure. The steps of FIG. 10 could be implemented by the proposed system 900 as illustrated in FIG. 9.

As shown in FIG. 10, the method 1000 may be construed as beginning at S1002, in which a schedule of training types is provided to a user. It should be noted that the schedule of training types includes information corresponding to a current training type, and the training types include at least two full-body training types, each of which is associated with exercising both the upper body and the lower body of the user.

A processor is then used to: obtain the motion readings reported from the inertial sensor and corresponding to the scheduled training types (S1004), receive the schedule of training types and a target status of a target training count or a target training time corresponding to each of the training types (S1006), and, determine the current training type based on the schedule of training types (S1008). Thereafter, a computing model is selected, based on the current training type, from computing models stored in a memory (S1010). Notably, each of the computing models defines a set of matching characteristics associated with a respective one of the training types, with the sets of matching characteristics associated with the at least two full-body training types sharing a common determination vector associated with the acceleration readings. The set of matching characteristics corresponding to the current training type and the motion readings are then compared until the target status has been attained for the current training type (S1012), after which a next training type is selected based on the schedule of training types (S1014).

Based on the next training type, another one of the computing models is selected (S1016). Then, activity information associated with the schedule of training types is determined (S1018), and an exercise amount of the user is computed based on the target status, the activity information, and the schedule of training types (S1020). In some embodiments, when the current training type is a full-body training type, computing of the exercise amount may involve: comparing the acceleration readings with the common determination vector and a determination threshold according to the selected one of the computing models corresponding to the current training type to provide a comparing result; incrementing an accumulated trigger count if the comparing result is positive unless a freeze condition occurs; and, computing the exercise amount based on the accumulated trigger count or the training time and the current training type.

Figure 11:
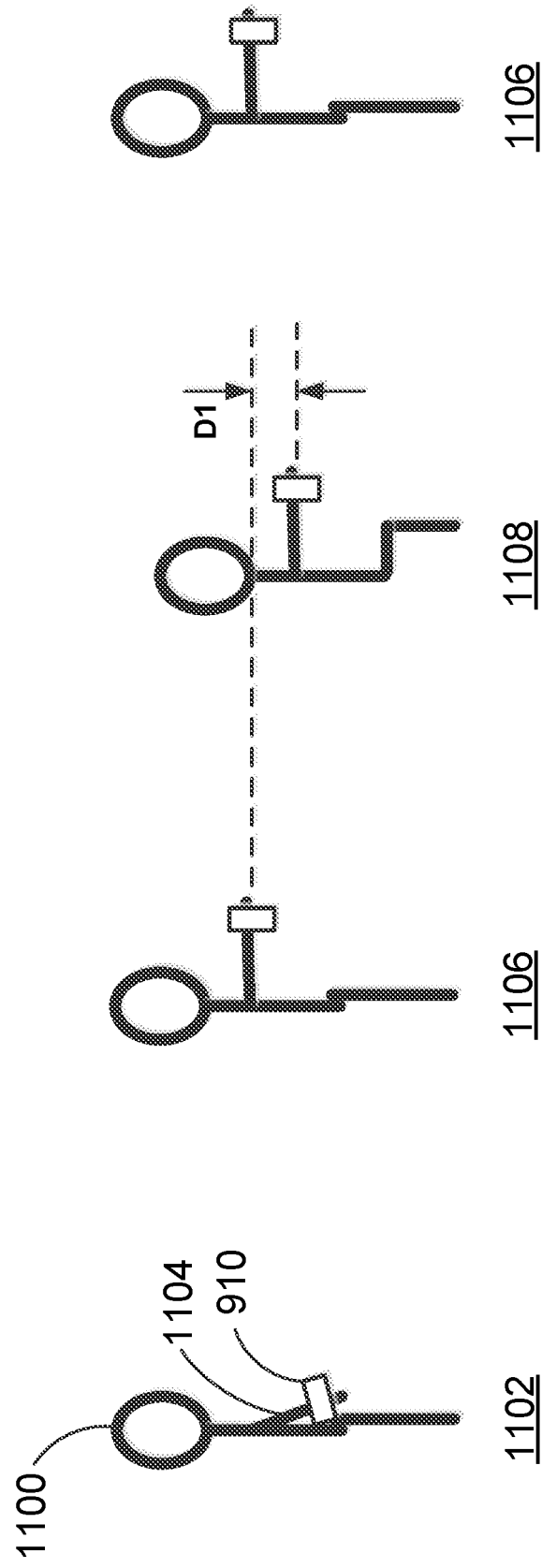
FIGS. 11A-11D illustrate performance of an example of a full-body training type in the form of a squat.

With respect to a full-body training type, an example of such a training type is depicted in FIGS. 11A-11D. In particular, these figures illustrate a squat training type. As shown in FIG. 11A, a user 1100 may be determined to be performing a squat based on a sequence of detected motion readings beginning with a standing pose 1102 exhibited in FIG. 11A, in which the user is standing with arms (e.g., arm 1104, the only one of which is depicted) being positioned at the user's sides and with the user wearing a wearable device (e.g., device 910 of FIG. 9). In FIG. 11B, motion readings associated with user 1100 extending arms to an arm-held-forward pose 1106 are detected. In FIG. 11C, a squat pose 1108, which includes the user moving to a seated position, is detected. In particular, in some embodiments, a moving (fall) distance (D1) along a downward direction is computed to determine whether squat pose 1108 is achieved. Then, as shown in FIG. 11D, user 1100 returns to the arm-held-forward pose 1106 to complete a count.

Figure 12:
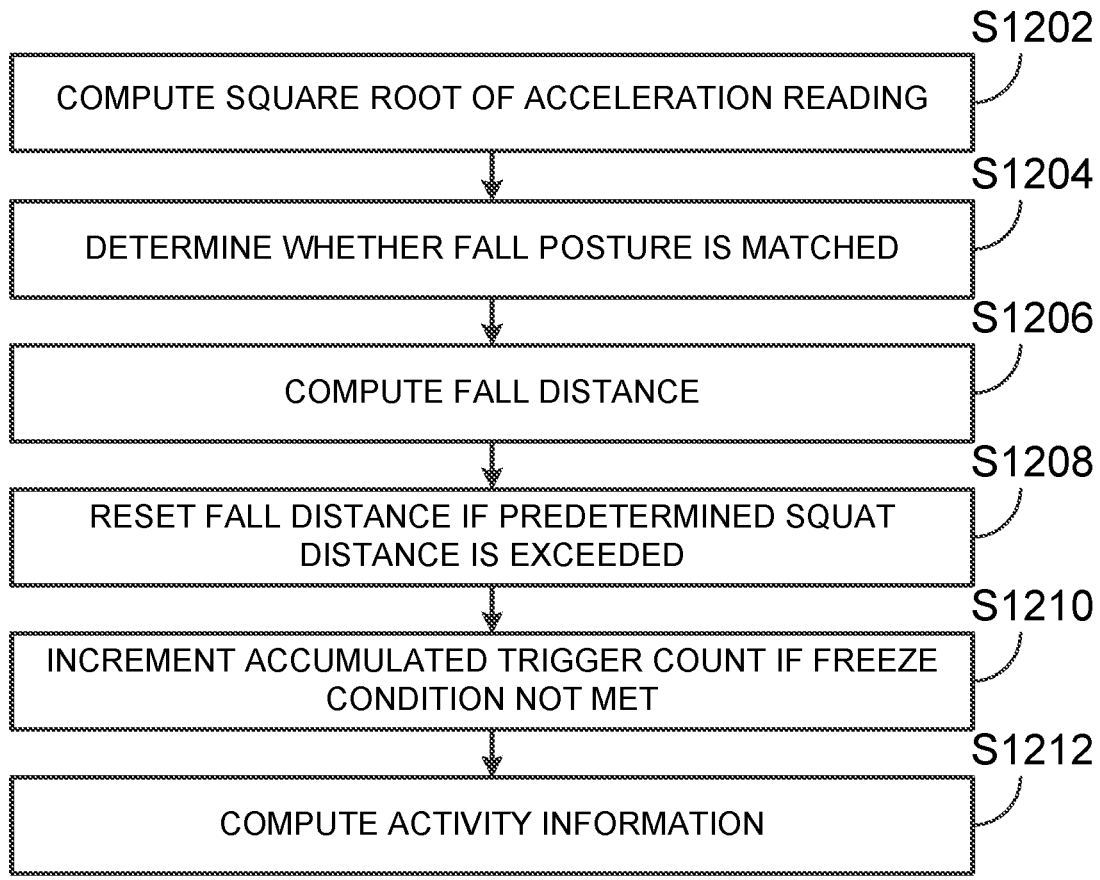
FIG. 12 illustrates a functional flowchart of a proposed method in accordance with one of the exemplary embodiments of the disclosure.

FIG. 12 illustrates a functional flowchart of a proposed method in accordance with one of the exemplary embodiments of the disclosure. The steps of FIG. 12 could be implemented by a processor for determining whether a squat has been performed as shown in FIGS. 11A-11D, for example.

As shown in FIG. 12, the method 1200 may be construed as beginning at S1202, in which a square root of the acceleration reading may be computed with respect to each of the x, y, and z axes to obtain a sum acceleration, and then a determination may be made as to whether a fall posture is matched (S1204). In some embodiments, this may be accomplished by detecting whether the sum acceleration is less than a low gravity threshold. In S1206, a fall distance (D1) may be computed based on a difference between the sum acceleration, a gravity value and a passed time during which the fall posture is matched. If the fall distance exceeds a predetermined squat distance, the fall distance may be reset (e.g., reset to zero) (S1208). Then, if a freeze condition does not occur after the reset of the fall distance, an accumulated trigger count may be incremented (S1210), and activity information may be computed based on the accumulated trigger count (S1212).

Figure 13:
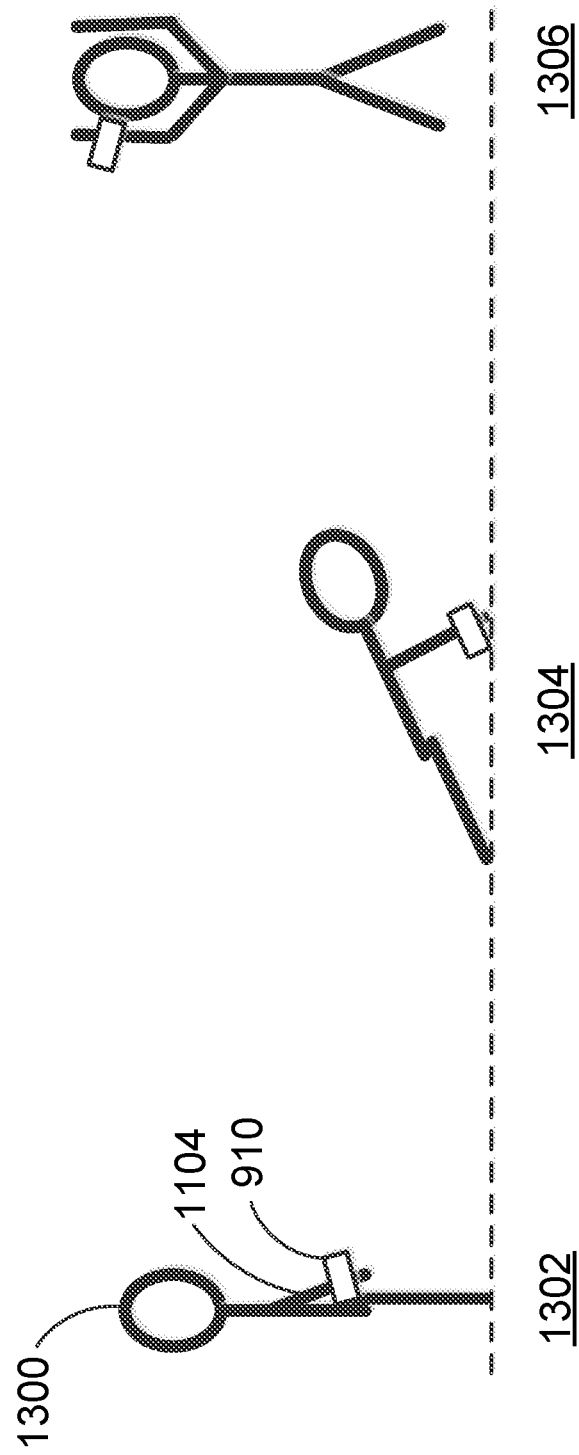
FIGS. 13A-13C illustrate performance of an example of a full-body training type in the form of a burpee.

Another example of a full-body training type, the burpee, is depicted in FIGS. 13A-13C. As shown, a user 1300 may be determined to be performing a burpee based on a sequence of detected motion readings beginning with a standing pose 1302 exhibited in FIG. 13A. It should be noted that when the pose remains static, the square root of an acceleration measurement along x, y, z direction would be equal to that of gravity (i.e., 9.8 m/s$^2$). In FIG. 13B, user 1300 is shown after moving to a push-up pose 1304, with direction of movement being indicated by the arrow. Determination of push-up pose 1304 may be based on a change of the acceleration measurement over a time span. After performing a push-up, user 1300 performs a jump (FIG. 13C), which may be determined by detection of increasing force (owing to the jump), which may indicate a peak (owing to a clapping motion) at the apex. User 1300 then returns to standing pose 1302 such as depicted in FIG. 13A.

Figure 14:
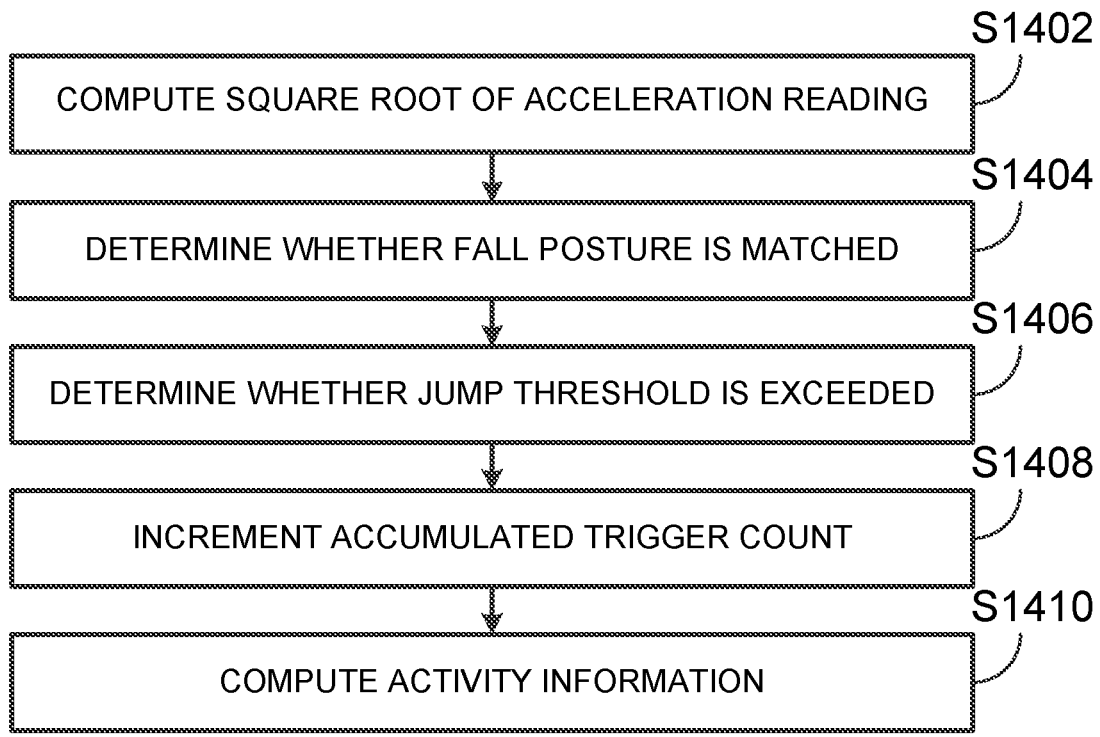
FIG. 14 illustrates a functional flowchart of a proposed method in accordance with one of the exemplary embodiments of the disclosure.

FIG. 14 illustrates a functional flowchart of a proposed method in accordance with one of the exemplary embodiments of the disclosure. The steps of FIG. 14 could be implemented by a processor for determining whether a burpee has been performed as shown in FIGS. 13A-13C, for example.

As shown in FIG. 14, the method may be construed as beginning at S1402, in which a square root of an acceleration reading is computed with respect to each of the x, y, and z axes to obtain a sum acceleration, and then a determination may be made as to whether a fall posture is matched (S1404). In some embodiments, this may be accomplished by detecting whether the sum acceleration is less than a low gravity threshold. In S1406, after determining that the fall posture has been matched, a determination may be made as to whether the sum acceleration exceeds a jump threshold. If the sum acceleration exceeds the jump threshold, the accumulated trigger count may be incremented (S1408), and activity information may be computed based on the accumulated trigger count (S1410).

The disclosure also provides a non-transitory computer readable medium, which records computer program to be loaded into any of the aforesaid processors to execute the steps of the proposed method. The computer program may be composed of a plurality of program instructions (for example, an organization chart, establishing program instruction, a table approving program instruction, a setting program instruction, and a deployment program instruction, etc), and these program instructions may be loaded into any of the aforesaid processors and executed by the same to accomplish various steps of the proposed method.

Various functions, functional components and/or blocks have been described herein. As will be appreciated by persons skilled in the art, the functional blocks will preferably be implemented through circuits (either dedicated circuits, or general purpose circuits, which operate under the control of one or more processors and coded instructions), which will typically comprise transistors or other circuit elements that are configured in such a way as to control the operation of the circuitry in accordance with the functions and operations described herein. As will be further appreciated, the specific structure or interconnections of the circuit elements will typically be determined by a compiler, such as a register transfer language (RTL) compiler. RTL compilers operate upon scripts that closely resemble assembly language code, to compile the script into a form that is used for the layout or fabrication of the ultimate circuitry. Indeed, RTL is well known for its role and use in the facilitation of the design process of electronic and digital systems.

No element, act, or instruction used in the detailed description of disclosed embodiments of the present application should be construed as geographically critical or essential to the disclosure unless explicitly described as such. Also, as used herein, each of the indefinite articles "a" and "an" can include more than one item. If only one item is intended, the terms "a single" or similar languages can be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:
1. A system, comprising:
a single wearable device configured to be worn by a user, the wearable device including an inertial sensor, having inertial sensor circuitry, configured to report motion readings based on motion of the inertial sensor, the inertial sensor including an accelerometer, having accelerometer circuitry, configured to generate acceleration readings;
a user interface having a notification device and a schedule-setting interface, the schedule-setting interface, having schedule-setting interface circuitry, being configured to provide a schedule of training types, the notification device, having notification device circuitry, being configured to provide a notification to the user based on the schedule of training types, the notification including information corresponding to a current training type from the schedule, the training types including at least two full-body training types, each of which is associated with exercising both the upper body and the lower body of the user;
a memory configured to store computing models, each of which defines a set of matching characteristics associated with a respective one of the training types, the sets of matching characteristics associated with the at least two full-body training types sharing a common vector associated with the acceleration readings; and
a processor, having processor circuitry, configured to:
obtain the motion readings reported from the inertial sensor and corresponding to the scheduled training types;

receive the schedule of training types and a target status of a target training count corresponding to each of the training types;

determine the current training type based on the schedule of training types;

select one of the computing models based on the current training type;

compare the set of matching characteristics corresponding to the current training type and the motion readings with respect to a determination threshold to distinguish between the training types sharing the common vector until the target status has been attained for the current training type;

select a next training type based on the schedule of training types;

select another one of the computing models based on the next training type;

determine activity information associated with the schedule of training types; and compute an exercise amount of the user based on the target status, the activity information, and the schedule of training types.

2. The system of claim 1, wherein, if the target status is the target training count, the processor is further configured to compare the set of matching characteristics corresponding to the current training type and the motion readings to determine a count based on a number of times the motion readings exhibit a matching pattern to the matching characteristics, and the activity information includes an exercise time during which the count accumulates and reaches the target training count.

3. The system of claim 1, wherein the processor is further configured to:

receive the schedule of training types and a target training time-corresponding to each of the training types; and if the target status is the target training time, compare the motion readings reported during the target training time and the set of matching characteristics corresponding to the current training type to determine a count based on a number of times the motion readings exhibit a matching pattern to the matching characteristics during the target training time, and the activity information includes the count determined.

4. The system of claim 1, wherein, in computing the exercise amount when the current training type is one of the at least two full-body training types, the processor is further configured to:

compare the acceleration readings with the common vector and the determination threshold according to the selected one of the computing models corresponding to the current training type to provide a comparing result;

increment an accumulated trigger count based on the comparing result unless a freeze condition occurs; and compute the exercise amount, with respect to the current training type, based on the accumulated trigger count or a training time and the current training type.

5. The system of claim 4, wherein the at least two full-body training types include squats and burpees.

6. The system of claim 5, wherein when the training type is squats, the processor is further configured to:

compute a square root of the acceleration readings with respect to each of x, y, and z axes to obtain a sum acceleration;

detect whether the sum acceleration is less than a low gravity threshold to determine whether a fall posture is matched;

compute a fall distance based on the sum acceleration, a gravity value and a passed time during which the fall posture is matched;

reset the fall distance to zero if the fall distance exceeds a predetermined squat distance;

increment the accumulated trigger count if the freeze condition does not occur after the reset of the fall distance; and compute the activity information based on the accumulated trigger count.

7. The system of claim 5, wherein when the training type is burpees, the processor is further configured to:

compute a square root of the acceleration readings with respect to each of x, y, and z axes to obtain a sum acceleration;

detect whether the sum acceleration is less than a low gravity threshold to determine whether a fall posture is matched;

after determining that the fall posture has been matched, detect whether the sum acceleration exceeds a jump threshold;

if the sum acceleration exceeds the jump threshold, increment the accumulated trigger count; and compute the activity information based on the accumulated trigger count.

8. The system of claim 1, wherein the schedule-setting interface is configured to receive a user input to select at least one of the training types in the schedule of training types.

9. The system of claim 1, wherein the exercise amount is expressed with respect to exercise strength exhibited by the upper body and the lower body of the user.

10. The system of claim 1, wherein the wearable device further comprises a heart rate sensor.

11. The system of claim 1, wherein:

the system further comprises a portable electronic device configured to communicate with the wearable device; and the portable electronic device houses the memory and the processor.

12. A method for using a single wearable device, the single wearable device configured to be worn by a user and including an inertial sensor, having inertial sensor circuitry, configured to report motion readings based on motion of the inertial sensor, the inertial sensor including an accelerometer, having accelerometer circuitry, configured to generate acceleration readings, the method comprising:

providing a schedule of training types to the user, the schedule of training types including information corresponding to a current training type, the training types including at least two full-body training types, each of which is associated with exercising both the upper body and the lower body of the user; and using a processor, having processor circuitry, to:

obtain the motion readings reported from the inertial sensor and corresponding to the scheduled training types;

receive the schedule of training types and a target status of a target training count corresponding to each of the training types;

determine the current training type based on the schedule of training types;

select a computing model, based on the current training type, from computing models stored in a memory, each of the computing models defining a set of matching characteristics associated with a respective one of the training types, the sets of matching characteristics associated with the at least two full-body training types sharing a common vector associated with the acceleration readings;

compare the set of matching characteristics corresponding to the current training type and the motion readings with respect to a determination threshold to distinguish between the training types sharing the common vector until the target status has been attained for the current training type;

select a next training type based on the schedule of training types;

select another one of the computing models based on the next training type;

determine activity information associated with the schedule of training types; and compute an exercise amount of the user based on the target status, the activity information, and the schedule of training types.

13. The method of claim 12, wherein the processor is further configured to:

receive the schedule of training types and a target training time corresponding to each of the training types; and if the target status is the target training count, compare the set of matching characteristics corresponding to the current training type and the motion readings to determine a count based on a number of times the motion readings exhibit a matching pattern to the matching characteristics, and the activity information includes an exercise time during which the count accumulates and reaches the target training count.

14. The method of claim 13, wherein, if the target status is the target training time, the processor is further used to compare the motion readings reported during the target training time and the set of matching characteristics corresponding to the current training type to determine a count based on a number of times the motion readings exhibit a matching pattern to the matching characteristics during the target training time, and the activity information includes the count determined.

15. The method of claim 12, wherein, in computing the exercise amount when the current training type is one of the at least two full-body training types, the processor is further configured to:

compare the acceleration readings with the common vector and a determination threshold according to the selected one of the computing models corresponding to the current training type to provide a comparing result;

increment an accumulated trigger count based on the comparing result unless a freeze condition occurs; and compute the exercise amount, with respect to the current training type, based on the accumulated trigger count or a training time and the current training type.

16. The method of claim 15, wherein the at least two full-body training types include squats and burpees.

17. The method of claim 16, wherein when the training type is squats, the processor is further used to:

compute a square root of the acceleration readings with respect to each of x, y, and z axes to obtain a sum acceleration;

detect whether the sum acceleration is less than a low gravity threshold to determine whether a fall posture is matched;

compute a fall distance based on the sum acceleration, a gravity value and a passed time during which the fall posture is matched;

reset the fall distance to zero if the fall distance exceeds a predetermined squat distance;

increment the accumulated trigger count if the freeze condition does not occur after the reset of the fall distance; and compute the activity information based on the accumulated trigger count.

18. The method of claim 16, wherein when the training type is burpees, the processor is further used to:

compute a square root of the acceleration readings with respect to each of x, y, and z axes to obtain a sum acceleration;

detect whether the sum acceleration is less than a low gravity threshold to determine whether a fall posture is matched;

after determining that the fall posture has been matched, detect whether the sum acceleration exceeds a jump threshold;

if the sum acceleration exceeds the jump threshold, increment the accumulated trigger count; and compute the activity information based on the accumulated trigger count.

19. The method of claim 12, wherein providing the schedule of training types to the user further comprises receiving, at the wearable device, a user input to select at least one of the training types in the schedule of training types.

20. The method of claim 12, wherein the exercise amount is expressed with respect to exercise strength exhibited by the upper body and the lower body of the user.

* * * * *